United States Patent [19]

Ovans

[11] Patent Number: 4,473,440

[45] Date of Patent: Sep. 25, 1984

[54] CALENDERED PEAT MOSS BOARD

[75] Inventor: Kevin J. Ovans, Cranbury, N.J.

[73] Assignee: Johnson & Johnson Inc., Montreal, Canada

[21] Appl. No.: 423,387

[22] Filed: Sep. 24, 1982

[51] Int. Cl.³ .............................................. D21H 5/12
[52] U.S. Cl. ................................ 162/148; 162/197; 162/205; 162/206
[58] Field of Search ................ 162/92, 148, 150, 197, 162/206, 205, 141, 142

[56] References Cited

U.S. PATENT DOCUMENTS

| | | | |
|---|---|---|---|
| 751,139 | 2/1904 | Beddies | 162/148 |
| 1,864,852 | 6/1932 | Oblinger | 162/206 |
| 2,229,401 | 1/1941 | Worm | 162/197 |

OTHER PUBLICATIONS

Casey, *Pulp and Paper*, 2nd Ed., vol. II, (1960) pp. 816, 817.

*Primary Examiner*—Peter Chin
*Attorney, Agent, or Firm*—Jason Lipow

[57] ABSTRACT

A peat moss containing board is manufactured by first conditioning the board to a specific water content and then densifying the board by calendering between rollers. A board of enhanced absorbency results.

7 Claims, 3 Drawing Figures

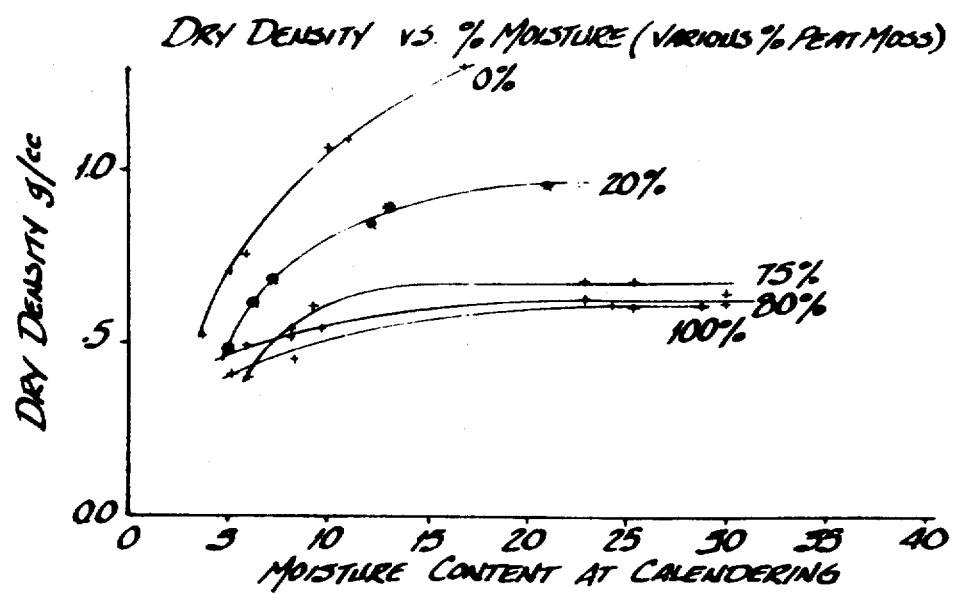

CALENDERED PEAT MOSS BOARD

BACKGROUND OF THE INVENTION

This invention relates to the manufacture of absorbent, flexible boards comprising peat moss and useful for incorporating into products such as diapers, sanitary napkins, tampons and the like as well as certain industrial uses wherein the properties of such peat moss boards are particularly useful.

The use of peat moss, in combination with other fibrous materials, for absorbent products has been suggested in U.S. Pat. No. 4,170,515 issued to J-M Lalancette, et al. on Oct. 9, 1979; in U.S. Pat. No. 4,226,237 issued to Y. Levesque on Oct. 7, 1980; and in U.S. Pat. No. 4,215,692, issued to Y. Levesque on Aug. 5, 1980.

Additionally, in a U.S. patent application, U.S. Ser. No. 377,532 filed on May 12, 1982 by Y. Levesque and commonly assigned herewith, it has been suggested that peat moss, in combination with mechanical wood pulp, be formed into a low density board, dried, and then compressed to form a thin, flexible, absorbent board which may be used directly in absorbent products.

These prior suggestions have introduced the use of peat moss as a substitute for the more conventionally employed absorbent materials thereby providing the art with a new source of material which is both economical and effective. In particular, the processing of peat moss into board form provides the manufacturer with this absorbent in a form that can be handled conveniently in processing equipment; a major consideration in the manufacture of the high volume, low cost products such as sanitary napkins, diapers and the like. In view of the relatively new concept of providing absorbent peat moss boards, it is expected that processes designed, in particular, to enhance the absorbency of the finished board are in an early state of development and that substantial improvement may be made in these processes to greatly increase the desirable properties of the finished boards. Accordingly, there is a need for improving the methods of manufacturing peat moss containing boards.

SUMMARY OF THE INVENTION

In accordance with this invention, a method is provide for greatly enhancing the absorbent properties of peat moss containing board and, in particular, board which is calendered after being formed to enhance its flexibility and suitability for absorbent products.

Specifically, a board comprising peat moss is formed by any of the methods described in the above cited U.S. Patents and applications. Typically, such board is formed by screening starting peat moss and combining the screened peat moss with other fibrous materials, e.g., wood pulp. An aqueous slurry is then formed from this mixture and flowed onto a Fourdrinier wire where the slurry is dewatered to form a low density board.

In accordance with this invention the formed board comprising peat moss is conditioned to have a water content which ranges between the values determined by the equation:

$$W = 0.10795P + 8.048 \pm 7.180$$

wherein W is the water content of the conditioned board, in weight percent and based on the weight of bone dry board; and P is the weight percent of peat moss based on the weight of the bone dry board. The so water conditioned board is then calendered to compress the board and produce a board of enhanced absorbency. It has been discovered that when the teachings of this invention are followed the resulting product has a high water absorbency and the ability to remain flexible prior to its use in absorbent products and while still dry. On the other hand, if the board is calendered while too dry; as has been heretofore suggested, the resulting product is brittle, tends to dust and sheets made therefrom tend to curl. When the board is calendered while too wet, the board sticks to the calender roll, becomes gel like or glassy, curls severly and, upon drying, becomes brittle.

The prescribed limitation with respect to water content while calendering apply throughout a wide range of peat moss concentrations, varying from 100% by weight of peat moss down through 20% by weight or less. As the weight percent of peat moss decreases much below the 20% level the board behaves essentially as non-peat moss containing board in that the enhancement in absorption properties with controlled moisture during calendering is no longer manifested.

BRIEF DESCRIPTION OF THE DRAWINGS

The invention will be best understood by a consideration of the following description taken together with the following drawings in which:

FIG. 3 is graphical depiction of the dry density of boards, made in accordance with this invention and having varying concentrations of peat moss, as a function of moisture content of the boards when calendering.

DETAILED DESCRIPTION OF THE INVENTION

Figure 1:
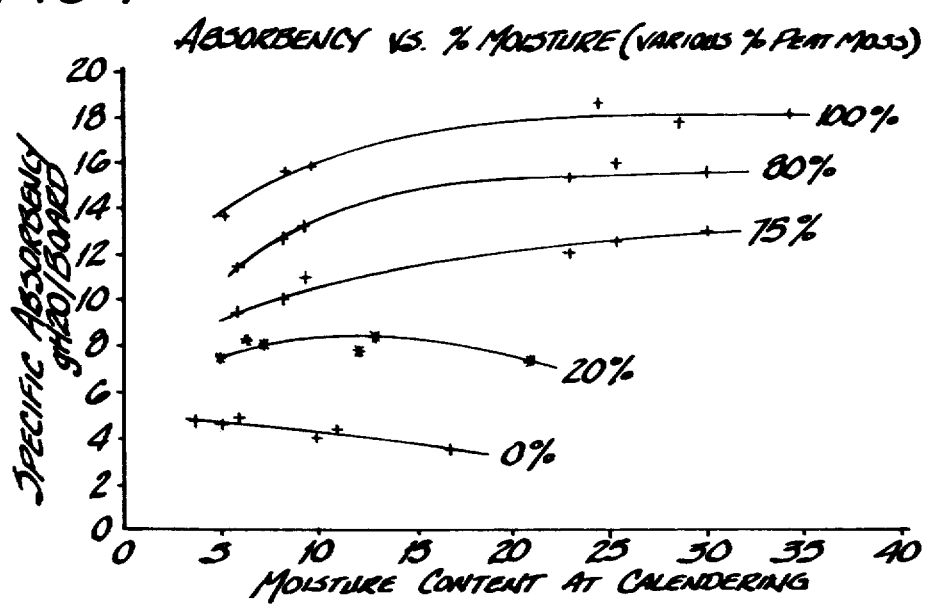
FIG. 1 is a graphical depiction of the specific absorbency of boards, made in accordance with this invention and having varying concentrations of peat moss, as a function of moisture content of the boards when calendering.

The starting peat moss is preferably of the sphagnum type and is capable of absorbing at least about 15 and preferably about 20 times its weight in water. Such peat moss is first screened to remove materials such as roots and branches which are discarded. Preferably, the remaining material is then separated into a usable fraction and peat fines. Such usable fraction is generally that portion remaining on a 100 mesh screen.

The screened peat moss fraction may be combined with other absorbent materials, preferably fibrous and cellulosic in nature and includes such materials as Kraft wood pulp and mechanical wood pulp. As used herein the term mechanical wood pulps is meant to include ground wood pulp, thermomechanical pulp and refiner wood pulp. Groundwood is essentially trees and branches which have been debarked, cleaned and then ground into particulate matter. Refiner woodpulp differs from groundwood pulp only in that the grinding step utilizes a refiner, i.e., a disk-like device well known in the art and generally having metalic ribs at the peripheral sections thereof which last contact the wood particles and help separate the wood fibers without excessively damaging them. Thermomechanical wood pulp is similar to refiner pulp with the exception that the wood particles are heated when in the refiner, usually with steam, and this heating further aids in separating the wood fibers. The common characteristic of these mechanical pulps is that no attempt has been made to separate the fibers by chemical means although they may later, after being reduced to fine particulate matter, be subjected to chemical treatment, e.g., bleaching.

Preferably, when the mechanical wood pulp is used in the board of this invention such mechanical wood pulp has a Canadian Standard Freeness (TAPPI TEST METHOD T-227) of from about 60–500 and preferably from about 150–300.

The Kraft wood pulp, also usable in combination with the peat moss and mechanical wood pulp is essentially a chemically treated, long fibered pulp such as sulphite and sulphate wood pulps. A suitable mixture of ingredients for the boards of this invention may comprise from 5 to about 20% by weight of mechanical wood pulp and from 5 to about 20% by weight of Kraft wood pulp, with the remainder being essentially the peat moss. It will be appreciated that while the above set out proportions are particularly useful for boards to be used for absorbent products, the invention is equally applicable to a wider range of peat moss concentrations and in fact is applicable to concentration of peat moss ranging from 20% by weight to 100% by weight.

The mixture of screened peat moss and fibers of cellulose, where employed, are slurried together to form an aqueous slurry which is to be flowed onto a Fourdrinier wire and dewatered to form the starting board. The slurry may range from about 0.1 to about 1.0% solids and other ingredients may be added to the slurry such as, for example coloring agents, wetting agents, adhesives, or the like. After passing the slurry onto the Fourdrinier wire, initial dewatering may take place under the influence of vacuum to render the water content to about 5 parts by weight of water per part by weight of solids.

The density of the board may be controlled by varying such factors as the pressure difference during the vacuum dewatering and the speed of Fourdrinier Wire. Generally, decreased vacuum and increased speed will result in a less dense product. A suitable low density peat moss board can be produced with a board lay down of from 15 to 35 grams of solid per square foot of board and for a vacuum pressure of from 10 to 15 inches of mercury. The speed of the Fourdrinier wire and the width of the vacuum slot under which the board is exposed to the pressure differential of the vacuum should be varied so as to create a residence time of the board over the vacuum slots of about 1 to about 5 seconds. For example, with 2 slots each having a ⅜ inch width, a Fourdrinier wire speed of about 2.5 feet per minute results in a residence time of about 1.5 seconds which, with a lay down of 20 grams per square foot, produces a low density board. Similarly, with 4 slots, each with a ⅜ inch width, a Fourdrinier speed of 1.7 feet per minute results in a residence time of 4.4 seconds and also produces a low density peat moss board. In each of the above examples, a vacuum of about 12 inches of mercury is maintained.

Irrespective of the choice of parameters chosen, the resulting board, prior to calendering is of low density, generally from about 0.03 to about 0.09 gm/cc. The presence of the mechanical wood pulp appears to advantageously enhance the porosity of the board which, in contrast to boards made without such mechanical wood pulp, has greater wettability and greater capillary suction capacity and has less tendency to dust, tear or otherwise behave adversely during processing.

In a specific embodiment of this invention, a laminate is made from the board and a layer of Kraft wood pulp. Preferably, the Kraft wood pulp is first laid down on a Fourdrinier wire from a slurry which can be about 0.1% solids. The Kraft slurry is dewatered and then passes to a second station where the peat moss and mechanical wood pulp mixture of this invention, in a slurry in the proportions described above, may be laid directly on top of the Kraft layer. This composite layer may be dewatered to produce a laminate of the low density peat moss board described herein having a layer of Kraft pulp adhered to its surface. It is preferred that the Kraft employed be bleached and have a Canadian Standard Freeness of relatively high value; e.g., about 500–1000. While the proportions of the Kraft layer to the peat moss board are not critical, a suitable product results when a layer of about 0.5 to 5.0 gms of Kraft pulp per foot square is employed. In addition, the strength characteristic of the laminate are greater than that which would result from the peat board if used alone.

In accordance with the teaching of the invention, the dewatered, low density board is conditioned to contain the herein prescribed moisture content prior to calendering. This moisture content conditioning can be accomplished by drying the low density board down to the prescribed moisture level and then calendering. The result product may then be further dried, in a second stage drier, or simply be allowed to equilibrate to its normal ambient water content. Alternatively, the dewatered board may be dried to ambient water content in a first stage drier and then water may be added, in a conditioning chamber, to increase the moisture content to a higher desired level.

While both methods will produce a board having the desirable absorbent properties discovered to innure to the moisture conditioning teachings herein, each method presents certain advantages and the choice will be determined by the manufacturer's weighing of these advantages. For example, by drying the dewatered board to the prescribed level in a first stage, calendering, and then final drying, there is an energy savings realized in the drying process in that the minimum amount of water is removed from the board. On the other hand, by drying to a low level and then adding water in a conditioning chamber, the process is more controllable and closer moisture content tolerances may be maintained.

Irrespective of how the dewatered board is conditioned, the moisture content prior to calendering should range between the values determined by the equation:

$$W = 0.10795P + 8.048 \pm 7.180$$

wherein W is the water content of the conditioned board, in weight percent and based on the weight of bone dry board; and P is the weight percent of the peat moss in the board, based on the weight of bone dry board. Preferably, the water contents should range between the narrower limits given by the following equation:

$$W = 0.11993P + 8.5106 \pm 2.85$$

wherein W and P have the meaning described above.

The conditioned board is next calendered between calender rollers. The calendering pressure may vary between 150 to 5000 pounds per linear inch and preferably between 500–1500 pounds per linear inch. If calendering is carried out at too low a pressure, the resulting board is bulky and unsuitable for direct use in absorbent products. On the other hand, too high calendering pressure produces a relatively unabsorbent board.

To illustrate the advantages of the invention, the following examples are given:

Example 1

Raw sphagnum peat moss is classified, using a Sweco classifier, into a peat fraction having a particle size falling between 10 and 48 mesh. The classified peat is combined with Kraft wood pulp having a Canadian Standard Freeness of 750 and groundwood having a Canadian Standard Freeness of 200, in the following proportions

| COMPONENTS | PARTS BY WEIGHT |
|---|---|
| Peat (10–48 mesh) | 80 |
| Kraft (750 CSF) | 10 |
| Groundwood (200 CSF) | 10 |

Boards are made from this solid mixture by dispersing the mixture in water to yield a slurry having a consistency of 1.2% by weight solids. One liter of the slurry is placed in a handsheet mold measuring 12 inches by 12 inches of the type manufactured by the Williams Apparatus Company of Watertown, N.Y. The slurry is diluted to a consistency of 0.15% by weight solids in accordance with the procedure set out in TAPPI Standard Method T-2050S71. After mixing thoroughly, the water is allowed to gravity drain, leaving a wet board of about 10.0%, by weight solids, which is then dried to form a board having a density of about 0.05 gm/cc. The board also contains 0.5%, by weight of dry material of a wetting agent. The wetting agent employed is a sodium dioctyl sulfo-succinate containing agent manufactured by the Rohm & Haas Company and sold by them under the trademark Triton GR-5.

The boards are conditioned to various moisture contents in a relative humidity chamber maintained at various relative humidities and then calendered under pressure of 6000 pounds per linear inch. Table 1 below sets out the visually observed characteristics of the boards as well as the specific absorbency. Specific absorbency is determined by a 30° plate test. This test is carried out by placing a 4 inch by 4 inch sample of the board between two transparent plates. The top plate has a port in flow communication with a liquid source (a 1% aqueous sodium chloride solution). The sample is allowed to absorb the liquid for 10 minutes until the sample is saturated under a confining pressure of 0.06 psi. The two plates and the confined saturated sample is then tilted at an angle of 30° from the horizontal and the sample is allowed to drain for 3 minutes. The weight of fluid absorbed is calculated. Specific absorbency is reported as weight of fluid absorbed divided by the weight of the base dry sample.

TABLE 1
VISUAL CHARACTERISTICS OF STANDARD BISHOP LAMINATE SAMPLES

| HUMIDITY | MOISTURE CONTENT | APPEARANCE BEFORE CALENDERING | APPEARANCE IMMEDIATELY AFTER CALENDARING | RECONDITIONED APPEARANCE | SPECIFIC ABSORBENCY (gm $H_2O$/gm board) | PERCENT DIFFERENCE |
|---|---|---|---|---|---|---|
| 0 | 5.7 | Very dusty, dry. | Very dusty, severe curl, calipre .027" Not sticky | Very dusty and unstable. Hard to do finishing, brittle. | 945 | — |
| 15 | 7.92 | Dusty, dry. curl, calipre .020" Not sticky | Dusty, severe but less severe. | Same as above | 1,000 | 5.8 |
| 23 | 9.80 | Dusty, dry. | Dusty, moderate curl, calipre .018" Not sticky | Manageable but dusty, somewhat brittle, possible but not ideal to do finishing. | 1,100 | 16.4 |
| 40 | 14.50 | Slightly dusty, slightly moist. | Slightly dusty no curl, calipre .016", very slightly sticky. | Flexible and only slightly dusty, good for finishing. | 1,130 | 19.8 |
| 65 | 23.00 | Very slightly dusty, moist. | Very slightly dusty, slight curl, calipre .016", some stickness | Flexible, very good for finishing but slight curl. | 1,200 | 27.0 |
| 75 | 26.00 | Not dusty, very moist. | Not dusty, severe curl, calipre .017" sticks, glassy. | Somewhat brittle, hard to finish, curl more severe. | 1,260 | 33.3 |
| 86 | 38.00 | Not dusty, very moist. | Not dusty, severe curl, calipre .027" severe sticking, very glassy. | Very brittle, impossible to do finishing, very severe curl. | 1,300 | 37.6 |

As can be seen from the above table, it is only in the mid range of moisture content that a board is obtained which is readily usable for further processing into an absorbent product. Absorbency is found to increase very rapidly with increasing moisture content and then somewhat less rapidly at the high moisture content levels.

Example 2

The procedures of Example 1 are followed to produce a series of boards calendered at various moisture contents and contain various weight percentages of peat moss. In each of these cases, the board comprised peat moss and Kraft wood pulp only. These boards are all calendered at a calendering pressure of 1250 pounds per linear inch. A sample containing no peat moss is also included as a control. The resulting boards are tested for specific absorbency and measurements are made of their bulk volume per gram when fully saturated with water as well as their dry density, i.e., the density of the calendered board at ambient conditions.

FIG. 1 illustrates the specific absorbency of the boards as a function of moisture content at calendering for the various peat moss concentrations. As can be seen, for the higher peat moss concentrations, a substantial increase in specific absorbency is noted as moisture content is increased until a relatively constant specific absorbency is reached. This effect is clearly peculiar to peat moss containing boards and disappears entirely when the peat moss content is reduced to 0%.

Figure 2:
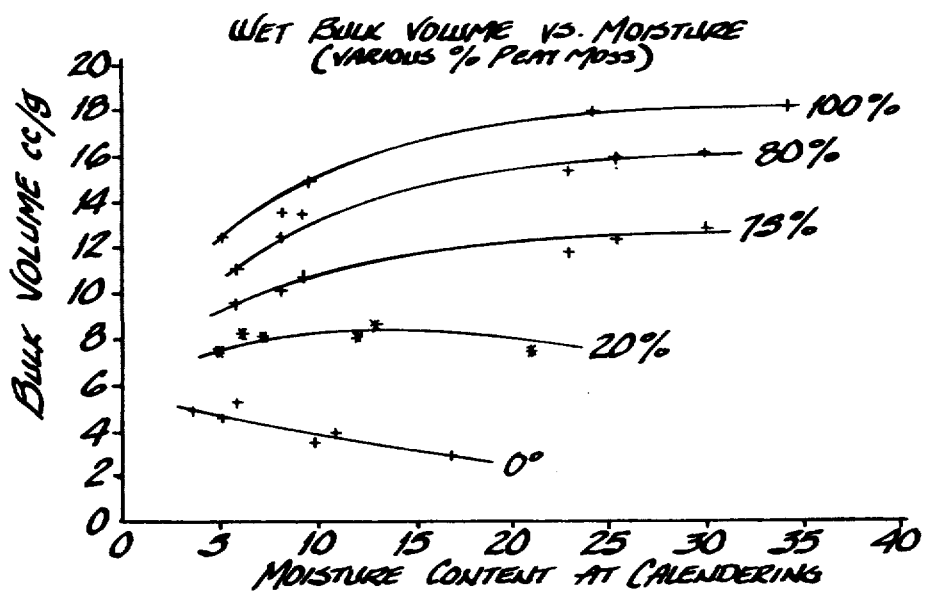
FIG. 2 is a graphical depiction of the bulk volume of boards, made in accordance with this invention and having varying concentrations of peat moss, as a function of moisture content of the boards when calendering.

FIG. 2 illustrates the concommitment variations in bulk volume which follows the relationship set out above in connection with FIG. 1.

FIG. 3 illustrates the variation in dry density of the calendered boards as functions of peat moss content and moisture content. To a degree, the lower density reflects the desirable property of board flexibility and as can be seen, at the higher peat moss contents, the dry density remains low irrespective of the moisture content at calendering. On the other hand, at 0% peat moss, increasing moisture content results in a relatively dense, inflexible board.

What is claimed is:

1. A process for manufacturing a calendered peat moss board having an enhanced absorbency of at least 8 grams of water per gram of board comprising:

forming a board comprising at least 20% by weight of peat moss;

conditioning said board to have a water content which ranges between the values determined by the following equation $$W = 0.10795 P + 8.048 \pm 7.180$$

wherein W is the water content of the conditioned board in weight percent based on the weight of bone dry board and P is the weight percent of the peat moss based on the weight of bone dry board; and calendering said conditioned board to form the calendered board of enhanced absorbency.

2. The method of claim 1 wherein said board is conditioned to have a water content which ranges between the values determined by the following equation:

$$W = 0.11993 P + 8.5106 \pm 2.85$$

wherein W is the water content of the conditioned board, in weight percent based on the weight of bone dry board and P is the weight percent of peat moss based on the weight of bone dry board.

3. The method of claim 1 wherein said conditioned board is calendered at a pressure of from about 150 to about 5000 pounds per linear inch.

4. The method of claim 3 wherein said conditioned board is calendered at a pressure of from about 500 to about 1500 pounds per linear inch.

5. The method of claim 1 wherein the board is formed from a water slurry, dewatered by imposing a pressure differential across the board and then conditioned by drying to said range of water content.

6. The method of claim 5 wherein said calendered board is then dried to ambient water content.

7. The method of claim 1 wherein said board is formed from a water slurry, dewatered, and then dried to below said range of water content; said dried board then conditioned in a conditioning chamber to said range of water content prior to calendering.

* * * * *